United States Patent [19]

Detwiler et al.

[11] Patent Number: 5,429,932
[45] Date of Patent: Jul. 4, 1995

[54] MULTILAYER ANALYTICAL ELEMENT CONTAINING NIACINAMIDE AND METHOD FOR THE DETERMINATION OF ETHANOL

[75] Inventors: Richard L. Detwiler, Webster; Robert J. Ferris, Rochester, both of N.Y.

[73] Assignee: Eastman Kodak Company, Rochester, N.Y.

[21] Appl. No.: 66,294

[22] Filed: May 24, 1993

[51] Int. Cl.$^6$ .......................... G12Q 1/32; G01N 33/00
[52] U.S. Cl. ............................................ 435/26; 435/4; 435/182; 436/106; 436/132; 422/57; 422/60
[58] Field of Search ...................... 435/26, 4, 25, 182, 435/190; 436/106, 111, 128, 132; 422/56, 57, 60

[56] References Cited

U.S. PATENT DOCUMENTS

| | | | |
|---|---|---|---|
| 3,926,736 | 12/1975 | Bucolo | 435/26 |
| 4,481,292 | 11/1984 | Raymond | 435/147 |
| 4,810,633 | 3/1989 | Bauer et al. | 435/25 |
| 4,889,797 | 12/1989 | Amano et al. | 435/4 |
| 5,086,143 | 2/1992 | Sutton et al. | 526/320 |
| 5,112,741 | 5/1992 | Palmer et al. | 435/25 |
| 5,141,854 | 8/1992 | Kaufman et al. | 435/26 |

FOREIGN PATENT DOCUMENTS 0464942 1/1992 European Pat. Off. .

OTHER PUBLICATIONS

Sigma Catalog 1993 —Diagnostic Reagents—under the heading of Alcohol. (Ethanol).
The Merck Index, 8th Edition, p. 729, 1968.

*Primary Examiner*—Michael G. Wityshyn
*Assistant Examiner*—Abdel A. Mohamed

[57] ABSTRACT

A multilayer analytical element has been prepared for accurate and rapid colorimetric determination of ethanol in aqueous specimens using alcohol dehydogenase and an oxidized nicotinamide coenzyme. The element includes two reagent layers beneath a porous spreading layer. The element also contains niacinamide in one or more layers to reduce the interference from alcohols other than ethanol.

19 Claims, No Drawings

MULTILAYER ANALYTICAL ELEMENT CONTAINING NIACINAMIDE AND METHOD FOR THE DETERMINATION OF ETHANOL

FIELD OF THE INVENTION

This invention relates to clinical chemistry. In particular, it relates to a multilayer analytical element and method for the quantitative determination of ethanol.

BACKGROUND OF THE INVENTION

Ethanol is a commonly encountered toxic substance. Methods for qualitative and quantitative determination of ethanol in body fluids, particularly human body fluids, are used in medicine and in law enforcement. In medicine, the level of ethanol in the blood is significant in diagnosing liver malfunction and alcoholism, as well as for understanding the reason for an emergency room patient being comatose. In law enforcement, such assays are used to determine whether or not an automobile operator is driving under the influence of alcohol.

Ethanol testing can be accomplished using both enzymatic and nonenzymatic assays. The nonenzymatic assays have a number of disadvantages and are being widely replaced by enzymatic assays which are more accurate, highly specific, more sensitive and require less expensive procedures. Enzymatic assays are generally based on the use of alcohol dehydrogenase to catalyze the reaction of ethanol to acetaldehyde. This reaction can be used alone, or in combination with other reactions to produce a spectrophotometric signal which can be related to the amount of ethanol in the tested specimen.

One enzymatic assay is based on the direct measurement of the reduced coenzyme (NADH), such as that described in U.S. Pat. No. 3,926,736 (Bucolo). This assay is carried out entirely in solution.

Another enzymatic assay is described in EP-A-0 464 942 (published Jan. 1, 1992) which uses nicotinamide adenine dinucleotide (NAD+) as a coenzyme with alcohol dehydrogenase to produce the reduced form of the coenzyme. The coenzyme, in turn, reacts wit a tetrazolium salt to produce a detectable dye. The described assay is carried out in a multilayer analytical element containing tris(hydroxymethyl)aminomethane buffer and both crosslinked and uncrosslinked gelatin layers.

One problem that has been encountered in developing a dry analytical element for the assay of ethanol is the strong interference by fluoride ion present in human serum. Fluoride ion is commonly used as a preservative in serum, and interferes in assays possibly by altering the equilibrium between ethanol and acetaldehyde, and causes the assay results to be biased positively compared to the true value of ethanol in the specimen. This problem has been effectively solved using a multilayer analytical element containing a high amount of buffer which is arranged in certain layers. Moreover, this element typically contains crosslinked gelatin as a binder for one or more of the reagent layers. Further details of such elements are found in U.S. Ser. No. 08/005,683 (filed Jan. 19, 1993 by Detwiler) which is entitled MULTILAYER ANALYTICAL ELEMENT CONTAINING PRIMARY AMINE BUFFER AND METHOD FOR THE DETERMINATION OF ETHANOL.

While the element just described can be used effectively to detect ethanol, it is understood that alcohol dehydrogenase is not 100% specific for ethanol. Thus, it also acts on some other alcohols, such as isopropanol and ethylene glycol, as substrates as well. Because of this reduced specificity for ethanol, other alcohols can act as interferents in an assay for ethanol. It would be highly desirable to reduce or eliminate those interferences.

SUMMARY OF THE INVENTION

A highly effective analytical element useful for the determination of ethanol has been prepared which exhibits reduced interferences from other alcohols. This element comprises a support having thereon, in order and in fluid contact:
  a) a first reagent layer containing a buffer having a primary amine, the buffer maintaining the pH at from about 8 to about 10 during an assay for ethanol, and the buffer being admixed with a first hydrophilic binder,
  b) a second reagent layer containing alcohol dehydrogenase and a buffer which is the same as that in the first reagent layer, the alcohol dehydrogenase and buffer being admixed with a second hydrophilic binder, and
  c) a porous spreading layer containing an oxidized nicotinamide coenzyme,
  the element further containing, in one or more layers, at least about 2 g/m$^2$ of niacinamide.

This invention also provides a method for the detection of ethanol comprising:
  A) contacting an aqueous fluid suspected of containing ethanol with the analytical element described above, and
  B) detecting the absorbance of the reduced form of the nicotinamide coenzyme as an indication of the presence of ethanol in the aqueous fluid.

Further a method for the detection of ethanol in a fluid sample comprises:
  A) at a pH of from about 8 to about 10, contacting a fluid sample suspected of containing ethanol with alcohol dehydrogenase, an oxidized nicotinamide coenzyme and niacinamide present in an amount of at least about 2 molar, and
  B) measuring the absorbance of the reduced form of the nicotinamide coenzyme as an indication of the presence of ethanol in the fluid sample.

The present invention provides a dry analytical element for the effective and specific detection of ethanol in a relatively short time using a signal generated by the reduction of a nicotinamide coenzyme by alcohol dehydrogenase. Interference by other alcohols has been effectively avoided by including niacinamide within the element.

The reduction of interferences from other alcohols can also be accomplished in solution assays. Thus, the methods of the present invention can be carried out in both solution and dry formats.

DETAILED DESCRIPTION OF THE INVENTION

The element of this invention can be used to determine (that is, detect either the presence, amount or both) ethanol in biological fluids of animals or humans, but preferably in humans. Such fluids include, but are not limited to, whole blood, plasma, sera, lymph, bile, urine, semen, cerebral spinal fluid, spinal fluid, sputum, perspiration, synovial fluid, lacrimal fluid and stool specimens as well as other biological fluids readily apparent to one skilled in the art. Fluid preparations of tissues can also be assayed. Preferably, human serum is assayed with this invention.

In its broadest embodiment, the dry element of this invention has an inert support with two or more reagent layers and a porous spreading layer disposed thereon. The support is generally dimensionally stable, inert to chemical reaction and preferably transparent (that is, radiation transmissive for wavelengths between about 200 and 900 nm). However, non-transparent supports can be used if the mode of detection is reflectance spectroscopy instead of transmission spectroscopy. Useful supports are well known in the art, and include but are not limited to polyesters, papers, metal foils and polystyrene, polycarbonates and cellulose esters.

The porous spreading zone is prepared from any of the known materials used for such zones as described, for example in U.S. Pat. Nos. 4,292,272 (Kitajima et al), 3,992,158 (Przybylowicz et al), 4,258,001 (Pierce et al) 4,430,436 (Koyama et al), and JP 57(1982)-101760 (published Jun. 24, 1982). It is desired that the spreading zone be isotropically porous, meaning that the porosity is the same in each direction in the zone as caused by interconnected spaces or pores between particles, fibers or polymeric strands.

Preferred spreading zones are those described in U.S. Pat. No. 3,992,158 as "blush polymer" zones. Such zones can be formed on a supporting material by dissolving a polymer in a mixture of two organic liquids, one of which is a lower boiling, good solvent for the polymer and other being a high boiling, non-solvent or poor solvent for the polymer. The resulting polymer formulation is coated on the supporting material and dried under controlled conditions to leave an isotropically porous zone. Various polymers are known to be useful in this context including, but not limited to, polycarbonates, polyamides, polyurethanes and cellulose esters such as cellulose acetate (which is preferred).

Within the porous zone can be incorporated particulate materials of various sizes to enhance the void volume. Useful particulate materials include, but are not limited to, inorganic pigments such as titanium dioxide, barium sulfate, zinc oxide and lead oxide, with barium sulfate and titanium dioxide being preferred. Further details of the preparation of "blush polymers" are described in U.S. Pat. No. 3,992,158 (noted above).

The elements have at least two other layers which can contain one or more reagents needed for the assay. All of the layers are generally in fluid contact with each other, meaning that fluids, reagents and reagent products can pass or be transported between superposed regions of adjacent layers, unless of course, a reagent is immobilized in some manner so it will not migrate within or without a layer.

The reagent layers of the element are composed of one or more hydrophilic binders [such as gelatin and other colloidal materials, hydrophilic binders such as poly(vinyl alcohol), acrylamide polymers, vinylpyrrolidone polymers and others known in the art, or mixtures thereof]. The same or different binders can be used in the individual reagent layers. In some embodiments, the binders are uncrosslinked, while in other embodiments, the binders are crosslinked, such as hardened gelatin. Gelatin is a preferred binder for both reagent layers.

In one embodiment, the binder in the first reagent layer is a crosslinked synthetic polymer which is prepared by conventional addition polymerization from two or three ethylenically unsaturated polymerizable monomers, as described in copending and commonly assigned U.S. Ser. No. 08/066,291, filed on even date herewith by Detwiler, Hasselberg and Ponticello and entitled MULTILAYER ANALYTICAL ELEMENT CONTAINING CROSSLINKED BINDER AND METHOD FOR THE DETERMINATION OF ETHANOL.

One type of monomer useful in preparing such crosslinked polymers is an acrylamide or a vinyl pyrrolidone. Mixtures of either or both are also useful. Acrylamides include, but are not limited to, acrylamide, N-isopropylacrylamide, N-(1,1-dimethyl-3-oxobutyl)acrylamide, 2-acrylamido-2-hydroxymethyl-1,3-propanediol, N-(3-dimethylaminopropyl)acrylamide, N,N-dimethylacrylamide, N,N-diethylacrylamide, 3-(2-dimethylaminoethyl)acrylamide and others readily apparent to one skilled in the art. The corresponding methacrylamides are also included. Acrylamide is preferred.

Vinyl pyrrolidones (or mixture thereof) include, but are not limited to, N-vinyl-2-pyrrolidone and others readily apparent to one skilled in the art. N-vinyl-2-pyrrolidone is preferred.

The amount of acrylamide or vinyl pyrrolidone useful in preparing the polymers is from about 90 to about 99.8 weight percent, with from about 96.5 to about 99 weight percent being preferred. All monomers weight percentages are based on total weight of monomers.

Preferably, both an acrylamide and a vinyl pyrrolidone are copolymerized to prepare the crosslinkable polymer. In such embodiments, preferably from about 40 to about 60 weight percent of an acrylamide, and from about 40 to about 60 weight percent of a vinyl pyrrolidone are used.

The second type of monomer is a crosslinkable monomer having a halomethylcarbonyl, haloethylcarbonyl, halomethylsulfonyl or halothylsulfonyl group which is crosslinkable with a diamine or dithiol. Useful monomers having halomethylcarbonyl or haloethylcarbonyl groups, which are preferred, include, but are not limited to, vinyl chloroacetate, N-(3-chloroacetamidopropyl)-methacrylamide, 2-chloroacetamidoethyl methacrylate, 4-chloroacetamidostyrene, 2-chloroacetamidocarbonyliminoethyl methacrylate, m- & p-chloroacetamidomethylstyrene, N-(3-chloroacetamidocarbonyliminopropyl)methacrylamide, 4-chloroacetamidocarbonyliminostyrene, m- & p-chloroacetamidocarbonyliminomethylstyrene, N-vinyl-N'-(3-chloropropionyl)urea, 4-(3-chloropropionamido)styrene, 4-(3-chloropropionamidocarbonylimino)styrene, 2-(3-chloropropionamido)ethyl methacrylate and N-[2-(3-chloropropionamido)ethyl]-methacrylamide. A most preferred monomer is N-(3-chloroacetamidopropyl)methacrylamide.

Monomers having crosslinkable halomethylsulfonyl or haloethylsulfonyl groups include, but are not limited to, m- & p-(2-chloroethylsulfonylmethyl)styrene, N-(4-chloroethylsulfonylmethylphenyl)acrylamide, N-[3-(2-chloroethylsulfonyl)propionamidomethylacrylamide, 2-{3-[2-(2-chloroethylsulfonyl)ethyl]propionyloxy}ethyl acrylate and others described in U.S. Pats. No. 4,161,407 (Campbell) and 4,548,870 (Ogawa et al).

The amount of the second type of monomer is generally from about 0.2 to about 10, and preferably from about 1 to about 3.5, weight percent.

It is well known that the haloethylsulfonyl and haloethylcarbonyl groups of polymers derived from monomers containing such groups can be readily dehydrohalogenated to vinylsulfonyl and vinylcarbonyl groups which are also readily crosslinkable with amine and sulfhydryl groups containing crosslinking agents in accordance with this invention, and such derived polymers are also within the scope of useful polymers of the present invention.

Useful crosslinking agents are compounds having two or more amino of sulfhydryl (or mercapto) groups, and include, but are not limited to, ethylenediamine, 1,3-propanediamine, 1,3-propanedithiol, dithiothreitol, dithioerythritol and butylenediamine. The amount of crosslinking agent is generally at from about 0.25 to about 1.5 equivalents, and preferably from about 0.5 to about 1.1 equivalents, per mole of hardening site in the polymer. Crosslinking is generally carried out during and immediately after the coating and drying operation.

The polymers described herein can be prepared using conventional addition polymerization techniques using redox initiator systems or organic soluble free radical generating initiating systems. The polymers are preferably prepared in solution using a redox initiator system and a mixture of water and isopropanol as the solvent.

Useful crosslinkable polymers include, but are not limited to, poly[acrylamide-co-N-vinyl-2-pyrrolidone-co-(3-chloroacetamidopropyl)methacrylamide], poly[acrylamide-co-N-vinyl-2-pyrrolidone-co-m & p-(2-chloroethylsulfonylmethyl)styrene], poly{acrylamide-co-N-vinyl-2-pyrrolidone-co-N-[4-(2-chloroethylsulfonylmethyl)phenyl]acrylamide}, poly[N-vinyl-2-pyrrolidone-co-N-(3-chloroacetamidopropyl)methacrylamide], poly[acrylamide-co-N-(3-chloroacetamidopropyl)methacrylamide], poly(acrylamide-co-N-vinyl-2-pyrrolidone-co-4-chloroacetamidostyrene). poly[acrylamide-co-N-vinyl- 2-pyrrolidone-co-4-(3-chloropropionamido)styrene], and poly(acrylamide-co-N-vinyl-2-pyrrolidone-co-4-chloroacetamidocarbonyliminostyrene).

The amount of crosslinked polymer in the first reagent layer will depend upon the amount of reagent to be dispersed, but is generally at least about 5 g/m$^2$, with from about 6 to about 15 g/m$^2$ being preferred.

When the elements contains a second reagent layer, the same or different (or mixtures thereof) binders can be therein. Alternative binders include gelatin (hardened or unhardened), poly(vinyl alcohol), acrylamide polymers, vinylpyrrolidone polymers or copolymers of acrylamide and a vinylpyrrolidone monomer. Gelatin is preferred in the second reagent layer.

The buffer used in the element (in both the first and second reagent layers) is one which has a primary amine and maintains the pH of the layers during an assay at from about 8 to about 10, and preferably at from about 8.5 to about 9. A number of such buffers are known and commercially available. They include, but are not limited to, tris (hydroxymethyl) aminomethane, tris(methyl)aminomethane, and their acid forms (addition salts of HCl, HF and the like), and tris (hydroxymethyl) aminomethane glutamate. Tris(hydroxymethyl)aminomethane or tris(hydroxymethyl)aminomethane hydrofluoride is preferred. The same or different buffers can be used in the layers of the element.

The amount of buffer in each reagent layer is generally at least about 25 mmoles/m$^2$, and from about 30 to about 50 mmoles/m$^2$ is preferred. It is not necessary, but it is preferred, that the amounts in multiple reagent layers be the same. For the preferred buffers, the preferred amount in each layer is about 41 mmoles/m$^2$ which corresponds to about 5 g/m$^2$.

The element also contains alcohol dehydrogenase which can be obtained from a number of commercial sources. Generally, the enzyme is present in an amount of from about 5000 to about 30,000 I.U./m$^2$. As used in this application, one I.U. represents the International Unit for enzyme activity and is defined as the amount of enzyme activity required to catalyze the conversion of 1 micromole of substrate per minute under standard pH and temperature conditions. For alcohol dehydrogenase, the standard conditions are 25° C. and a pH of about 8. Preferably, the enzyme is present within a second reagent layer.

Within the porous spreading layer is an oxidized nicotinamide coenzyme which can be reduced to provide a detectable colorimetric signal upon reaction with ethanol as catalyzed by alcohol dehydrogenase. Useful oxidized coenzymes include, but are not limited to, oxidized nicotinamide adenine dinucleotide (NAD+) and oxidized nicotinamide adenine dinucleotide phosphate (NADP+). For example, in the assay, NADH absorbs at about 340 nm, and NADPH absorbs at about 340 nm.

Optionally, but preferably, the porous spreading layer is separated from the reagent layers with a hydrophilic subbing layer composed of one or more suitable hydrophilic binder materials. Such materials include, but are not limited to gelatin and other colloidal materials, polymers of vinyl pyrrolidone, vinyl alcohol, acylamide, N-alkylsubstituted acrylamide (such as N-isopropylacrylamide), including copolymers thereof, and other materials readily apparent to one skilled in the art.

One or more layers of the element can also contain one or more useful materials, such as antioxidants, coating aids, surfactants, bacteriostats and other materials known in the art to facilitate coating of the layers, reagent stability and fluid spreading during the assay.

The interference from alcohols other than ethanol is reduced markedly by the inclusion of at least about 2 g/m$^2$ of niacinamide in the element of this invention. Preferably, there is from about 6 to about 20 g/m$^2$ of niacinamide in the element. Niacinamide (also known as nicotinamide, nicotinic acid amide or 3-pyridinecarboxylic acid amide), can be present in any number of the layers. Preferably, it is present in either the porous spreading layer or second reagent layer. Most preferably, it is in the porous spreading layer.

Niacinamide is available from a number of commercial sources, or it can be isolated from natural sources using known procedures [for example, Euler et al, Z.Physiol.Chem. 258, 212, (1939)], or prepared using synthetic procedures (for example, U.S. Pat. No. 2,993,051).

A variety of different elements, depending upon the method and equipment for assay, can be prepared in accordance with this invention. They can be configured in a variety of forms and shapes, including elongated tapes of any desired width, sheets, slides or chips. Preferred elements are configured as test slides like those commercially available under the EKTACHEM ™ trademark for a variety of clinical assays. Such test slides are described in a considerable number of patents and other publications. Generally, the layers are formed on a suitable support by applying specific aqueous or solvent-based formulations of individual layer compositions in sequence using suitable coating equipment, and procedures followed by drying.

In a preferred embodiment, a multilayer analytical element of this invention comprises a nonporous, transparent support having thereon, in order and in fluid contact:

a first reagent layer containing a buffer having a primary amine as defined above admixed with a first hydrophilic binder, a second reagent layer comprising alcohol dehydrogenase and the same buffer as described for the first reagent layer admixed with a second hydrophilic binder, a hydrophilic subbing layer, and a porous spreading layer containing an oxidized nicotinamide coenzyme and niacinamide as described above. The hydrophilic binders in the reagent layers can be the same or different.

The dry assay of this invention can be manual or automated. In general, the element is used by physically contacting it with the test specimen (for example, from 1 to 200 $\mu l$) suspected of containing ethanol under ambient conditions (although other temperatures can be used). The specimen and reagents become mixed within the layers of the element and any ethanol present in the specimen reacts with the oxidized nicotinamide coenzyme to produce the reduced form which is detectable as described above. Contact can be achieved in any suitable manner, for example by dipping or immersing the element into the specimen or preferably, by spotting the specimen onto the element by hand, machine or suitable dispensing means.

After specimen application, the element is exposed to any conditioning, such as incubation, heating or otherwise, that may be desirable to quicken or otherwise facilitate obtaining a test result.

Generally within about 5 minutes, a spectrophotometric measurement is made. This measurement can be made using suitable reflection or transmission spectrophotometric equipment and procedures as a measure of ethanol concentration in the test sample. Generally, the detectable signal is measured at a wavelength in the range of from about 320 to about 360 nm.

In the solution assay method of this invention, a fluid sample suspected of containing ethanol is contacted with alcohol dehydrogenase, an oxidized nicotinamide coenzyme and niacinamide. The components can be supplied in the same or different buffered solutions. The amount of niacinamide used in the assay is at least about 0.05 molar, and preferably from about 0.1 to about 0.4 molar.

The resulting mixture is buffered to a pH of from about 8.5 to about 10, and preferably from about 8 to about 9 using a suitable buffer. After about 5 minutes of incubation at room or higher temperature, the absorbance of the reduced form of the nicotinamide coenzyme is measured as an indication of the presence of ethanol in the fluid sample. Measurement can be achieved using suitable equipment.

The following examples are included to illustrate the practice of this invention, and are not meant to be limiting in any way. The materials used in the examples were obtained as follows:

ESTANE ™ 5715 polyurethane resin from B. F. Goodrich, TRITON ™ X-100 nonionic surfactant and TRITON ™ X-200E anionic surfactant from Rohm and Haas (rights now owned by Union Carbide), and the remainder of the materials from Eastman Kodak Company or other commercial sources, or they were prepared using standard procedures and readily available starting materials.

EXAMPLE 1

Preferred Analytical Element for Ethanol Determination

The preferred element of this invention and amounts of components are illustrated in the structure:

| | | Dry Coverage (g/m$^2$) |
|---|---|---|
| Spreading Layer | Barium sulfate | 105 |
| | Cellulose acetate | 8 |
| | ESTANE ™ 5715 polyurethane | 1.1 |
| | TRITON ™ X-405 nonionic surfactant | 2.1 |
| | NAD+ | 8 |
| | Niacinamide | 8 |
| Subbing Layer | Poly(N-isopropylacrylamide) | 0.4 |
| Second Reagent Layer | Gelatin (unhardened) | 6 |
| | Tris(hydroxymethyl)-aminomethane | 5 |
| | Ottasept | 0.02 |
| | TRITON ™ X-200E anionic surfactant | 0.01 |
| | TRITON ™ X-100 nonionic surfactant | 0.02 |
| | Alcohol dehydrogenase | 10,000* |
| | Bovine Serum Albumin | 1.75 |
| Interlayer | Gelatin | 1.1 |
| | Bis(vinylsulfonylmethyl) ether | 0.14 |
| | TRITON ™ X-200E anionic surfactant | 0.01 |
| | TRITON ™ X-100 nonionic surfactant | 0.02 |
| | Ottasept | 0.003 |
| First Reagent Layer | Gelatin | 6 |
| | TRITON ™ X-100 nonionic surfactant | 0.02 |
| | TRITON ™ X-200E anionic surfactant | 0.01 |
| | Ottasept | 0.02 |
| | Tris(hydroxymethyl)aminomethane | 5 |
| | Poly(ethylene terephthalate) Support | |

*I.U./m$^2$

EXAMPLES 2–5

Determination of Ethanol Using Dry Elements

These examples demonstrate the use of several elements of this invention and the reduction of interferences from various alcohols. Elements like those in Example 1 were prepared and used in these examples.

In Example 2, the amount of niacinamide in the elements was 0, 8 or 16 g/m$^2$, and the elements were buffered to a pH of 8.75. A base solution containing ethanol (100 mg/dl) was prepared. To portions (3 ml) of the base solution were added the following alcohols which were evaluated as interferents: isopropyl alcohol (700 mg/dl), ethylene glycol (800 mg/dl), N-propanol (200 mg/dl) and N-butanol (200 mg/dl). All of the resulting test solutions were assayed for ethanol using the elements containing various amounts of niacinamide. The difference in predicted ethanol concentration in the test solutions and the "blank" containing 100 mg/dl of ethanol is defined as the interference due to the alcohols other than ethanol.

The results for Example 2 are shown in the following Table I.

TABLE I

| Niacinamide (g/m²) | Interferences (mg/dl) | | | |
|---|---|---|---|---|
| | Isopropyl alcohol | Ethylene glycol | n-propanol | n-butanol |
| 0 | 56 | 12 | 118 | 61 |
| 8 | 28 | 3 | 95 | 42 |
| 16 | 12 | 2 | 77 | 21 |

The results indicate that the presence of niacinamide effectively reduces the interference from the various alcohols in the assay for ethanol.

Example 3 was carried out similarly to Example 2 except the elements were buffered to a pH of 8. The results are shown in the following Table II.

TABLE II

| Niacinamide (g/m²) | Interferences (mg/dl) | | | |
|---|---|---|---|---|
| | Isopropyl alcohol | Ethylene glycol | n-propanol | n-butanol |
| 0 | 74 | 14 | 110 | 63 |
| 8 | 48 | 7 | 102 | 49 |
| 16 | 16 | 1 | 74 | 28 |

Similarly, Example 4 was carried out using elements buffered to a pH of 8, but wherein the niacinamide was present in the second reagent layer only. The results are shown in Table III below.

TABLE III

| Niacinamide (g/m²) | Interferences (mg/dl) | | | |
|---|---|---|---|---|
| | Isopropyl alcohol | Ethylene glycol | n-propanol | n-butanol |
| 0 | 74 | 14 | 110 | 63 |
| 8 | 8 | 2 | 55 | 21 |

In Example 5, niacinamide was located in both the porous spreading, or in both the porous spreading and second reagent layers. The results are shown in Table IV below.

TABLE IV

| Niacinamide (g/m²) | Interferences (mg/dl) | | | |
|---|---|---|---|---|
| | Isopropyl alcohol | Ethylene glycol | n-propanol | n-butanol |
| 8,0* | 48 | 7 | 102 | 49 |
| 8,8* | 4 | 4 | 47 | 16 |

*First amount in the porous spreading layer. Second amount in the second reagent layer.

The invention has been described in detail with particular reference to preferred embodiments thereof, but it will be understood that variations and modifications can be effected within the spirit and scope of the invention. U.S. patents noted above are incorporated herein by reference for any disclosure considered pertinent and essential to the presently claimed invention.

We claim:

1. An analytical element for the determination of ethanol comprising a support having thereon, in order and in fluid contact:
   a) a first reagent layer containing a buffer having a primary amine, said buffer maintaining the pH at from about 8 to about 10 during an assay for ethanol, and said buffer being admixed with a first hydrophilic binder,
   b) a second reagent layer containing an alcohol dehydrogenase and a buffer which is the same as that in said first reagent layer, said alcohol dehydrogenase and buffer being admixed with a second hydrophilic binder, and
   c) a porous spreading layer containing an oxidized nicotinamide coenzyme,
   said element further containing, in one or more layers, at least 2 g/m² of niacinamide.

2. The element of claim 1 wherein said buffer in said first and second reagent layers is tris(hydroxymethyl)aminomethane, tris(methyl)aminomethane or tris(hydroxymethyl)aminomethane glutamate.

3. The element of claim 2 wherein said buffer in both of said reagent layers is tris(hydroxymethyl)aminomethane.

4. The element of claim 1 wherein said porous spreading layer is formed from a blush polymer.

5. The element of claim 1 wherein said first hydrophilic binder is gelatin.

6. The element of claim 1 wherein said first and second hydrophilic binders are the same.

7. The element of claim 6 wherein said first and second hydrophilic binders are gelatin.

8. The element of claim 1 wherein the niacinamide is present in an amount of from about 6 to about 20 g/m² in said porous spreading layer.

9. The element of claim 1 wherein said nicotinamide coenzyme is nicotinamide adenine dinucleotide.

10. The element of claim 1 further comprising an additional interlayer between said first and second reagent layers.

11. The element of claim 1 wherein said niacinamide is located in either said porous spreading layer or said second reagent layer.

12. A method for the detection of ethanol comprising:
   A) contacting an aqueous fluid suspected of containing ethanol with an analytical element comprising a support having thereon, in order and in fluid contact:
      a) a first reagent layer containing a buffer having a primary amine, said buffer maintaining the pH at from about 8 to about 10 during an assay for ethanol, and said buffer being admixed with a first hydrophilic binder,
      b) a second reagent layer containing an alcohol dehydrogenase and a buffer which is the same as that in said first reagent layer, said alcohol dehydrogenase and buffer being admixed with a second hydrophilic binder, and
      c) a porous spreading layer containing an oxidized nicotinamide coenzyme,
      said element further containing, in one or more layers, at least 2 g/m² of niacinamide, and
   B) detecting the absorbance of the reduced form of said nicotinamide coenzyme as an indication of the presence of ethanol in said aqueous fluid.

13. The method of claim 12 wherein said detection step B) is carried out within about 5 minutes of said contacting step A).

14. The method of claim 12 wherein said aqueous fluid is human whole blood, serum or plasma.

15. The method of claim 12 wherein said ethanol is detected from measuring the absorbance of the reduced form of nicotinamide adenine dinucleotide.

16. The method of claim 12 wherein said buffer in both of said reagent layers maintains the pH of said element at from about 8.5 to about 9.

17. A method for the detection of ethanol in a fluid sample comprising:

A) at a pH of from about 8 to about 10, contacting a fluid sample suspected of containing ethanol with an alcohol dehydrogenase, an oxidized nicotinamide coenzyme and niacinamide present in an amount of at least 0.05 molar, and B) measuring the absorbance of the reduced form of said nicotinamide coenzyme as an indication of the presence of ethanol in said fluid sample.

18. The method of claim 17 wherein said contacting step is carried out at a pH of from about 8.5 to about 9, and said nicotinamide coenzyme is nicotinamide adenine dinucleotide.

19. The method of claim 17 wherein niacinamide is present in an amount of from about 0.1 to about 0.4 molar.

* * * * *